United States Patent [19]
Akazawa et al.

[11] Patent Number: 5,480,649
[45] Date of Patent: Jan. 2, 1996

[54] PROCATEROL-CONTAINING PREPARATION FOR APPLICATION TO THE SKIN

[75] Inventors: Mitsuji Akazawa; Teruo Hama, both of Kagawa; Yukio Kimura; Yoshinobu Yasuda, both of Tokushima, all of Japan

[73] Assignee: Teikoku Seiaku Kabushiki Kaisha, Kagawa, Japan

[21] Appl. No.: 861,805

[22] PCT Filed: Nov. 7, 1991

[86] PCT No.: PCT/JP91/01527

§ 371 Date: Jun. 19, 1992

§ 102(e) Date: Jun. 19, 1992

[87] PCT Pub. No.: WO92/08449

PCT Pub. Date: May 29, 1992

[30] Foreign Application Priority Data

Nov. 9, 1990 [JP] Japan .................................. 2-305023

[51] Int. Cl.$^6$ .......................... A61L 15/58; A61L 15/44; A61K 9/10; A61K 9/70
[52] U.S. Cl. ........................ 424/449; 424/487; 424/448; 514/947
[58] Field of Search ................... 424/484, 487, 424/443, 447–449; 514/826, 947, 970; 428/424.2, 516–517, 520; 602/52, 54

[56] References Cited

U.S. PATENT DOCUMENTS

| | | | |
|---|---|---|---|
| 4,289,749 | 9/1981 | Keith et al. | 424/448 |
| 4,788,064 | 11/1988 | Patel et al. | 424/444 |
| 4,837,025 | 6/1989 | Guillemet et al. | 424/449 |
| 4,900,554 | 2/1990 | Yanagibashi et al. | 424/448 |

FOREIGN PATENT DOCUMENTS

| | | |
|---|---|---|
| 0055635 | 10/1981 | European Pat. Off. . |
| 0036138 | 8/1985 | European Pat. Off. . |
| 2345161 | 3/1976 | France . |
| 5517354 | 2/1980 | Japan . |
| 56-142209 | 11/1981 | Japan . |
| 58-43365 | 9/1983 | Japan . |
| 63-10716 | 1/1988 | Japan . |
| 63-150222 | 6/1988 | Japan . |
| 63-203613 | 8/1988 | Japan . |
| 63-203162 | 8/1988 | Japan . |
| 64-52727 | 2/1989 | Japan . |

OTHER PUBLICATIONS

Chemical Abstracts, vol. 87, No. 18, Oct. 31, 1977, Abstract No. 141303J, p. 330 & JP-A-7738016, Mar. 1977.
World Patents Index Latest, Derwent Publications, Ltd. London, GB; AN86-344273(52) & JP-A-61 260 014, Nov. 1986.
Patent Abstracts of Japan, vol. 08, No. 110 (C-224) May 23, 1984 & JP-A-59 025 320, Feb. 9, 1984.

*Primary Examiner*—Edward J. Webman

[57] ABSTRACT

A procaterol-containing preparation for application to the skin which comprises a drug-retaining layer provided on a support, wherein said drug-retaining layer comprises a substantially water-free adhesive gel base comprising as essential components polyacrylic acid, a crosslinking agent and at least one lower alcohol or polyvalent alcohol, and 0.1 to 5% by weight of procaterol or a pharmaceutically acceptable salt thereof. Said preparation for application to the skin can be used as an external preparation for application to the skin which is capable of stably delivering procaterol or a salt thereof through the skin for a long time of period.

23 Claims, 2 Drawing Sheets

PROCATEROL-CONTAINING PREPARATION FOR APPLICATION TO THE SKIN

TECHNICAL FIELD

The present invention relates to a procaterol-containing external preparation for application to the skin. More particularly, the present invention relates to an external preparation for application to the skin which comprises as active ingredients procaterol or a pharmaceutically acceptable salt thereof which is dissolved in an alcohol dispersedly in a substantially water-free polyacrylic acid gel, said preparation being capable of stably delivering said active ingredient through the skin for a long period of time.

BACKGROUND ART

Procaterol is known as a bronchodilator which stimulates the β-receptor of sympathetic nerves and shows strong bronchodilating activity in very small amounts. The duration of the activity of procaterol is long (8 hours or more), and hence, procaterol is an excellent drug from the viewpoint of duration of time and absorbability.

This drug is generally used in the form of a hydrochloride salt and orally administered in the form of tablets, granules, syrups or administered by inhalation in the form of inhalants or aerosols.

The present inventors have tried to transdermally administer procaterol in the form of conventional cataplasms or tapes in order to externally apply procaterol. However, the present inventors have found that such a preparation for application to the skin has the following disadvantages:

(1) The cataplasms should contain a fixed amount of a drug in a base so that the desired activity of the drug is exhibited. However, since the cataplasms is usually applied in a large amount (1,000 to 1,500 g/m$^2$), the drug present at the deep portion within the base moves hardly to the surface and is hardly absorbed, and as a result, the availability of the drug is lowered. Therefore, in case of a drug having a strong bronchodilating activity in a very small amount like procaterol, it is not preferable because of remaining of the drug within the base.

(2) On the other hand, when an aqueous base like the base for cataplasms is spread in such a thin layer as 50 to 300 g/m$^2$, it results in a decreased adhesiveness and an increased evaporation of water, which is not preferable in viewpoint of the properties required for the preparation for application to the skin.

(3) Procaterol can be used in the form of tapes. However, procaterol shows a strong interaction with the base of tapes, which is not preferable in viewpoint of the delivery and availability of the drug.

Under the circumstances, the present inventors have intensively studied for developing an improved preparation for application to the skin suitable for transdermal administration of procaterol. As a result, the present inventors have found that a quite novel preparations for application to the skin can be obtained by incorporating procaterol into a substantially water-free adhesive gel base prepared by dissolving polyacrylic acid in an alcohol and crosslinking polyacrylic acid with a crosslinking agent, and then have completed the present invention. The preparation of the present invention has the following characteristics:

(1) Since the preparation of the present invention contains a larger amount of alcohol in the base than that of conventional tapes or cataplasms, the drug is easily dissolved and dispersedly kept in the base, and hence, there can be prepared a base which allows an excellent drug delivery even when a small amount of the drug is contained in the base;

(2) Polyacrylic acid used in the base inhibits the decomposition of the drug, allowing a stable storage of the drug for a long period of time;

(3) Since the drug dissolved is dispersedly retained within the adhesive gel base, the drug is delivered to the skin at a constant rate, allowing a continuous transdermal absorption;

(4) Since the base contains substantially no water, it is stable and hardly denatured when applied to the skin or during storage; and (5) The preparation of the present invention has moderate adhesiveness, and hence, can be thinly applied. In addition, the preparation of the present invention does not cause pain when peeled off.

DISCLOSURE OF THE INVENTION

That is, the present invention provides a procaterol-containing external preparation for application to the skin which comprises a drug-retaining layer provided on a support, wherein said drug-retaining layer comprises an adhesive gel base comprising as essential components polyacrylic acid, a cross-linking agent and at least one lower alcohol or polyvalent alcohol, and 0.1 to 5% (.% by weight, hereinafter the same) of procaterol or a pharmaceutically acceptable salt thereof. Procaterol is contained in the network structure formed by the crosslinking agent with polyacrylic acid in the state of being dispersedly dissolved in the lower alcohol or polyvalent alcohol.

Polyacrylic acid used in the preparation for application to the skin of the present invention retains the lower alcohol or polyvalent alcohol which contains procaterol dissolved therein and provides a stable delivery of procaterol at the surface in contact with the skin. Polyacrylic acid also provides adhesiveness for the preparation, and hence, there can be obtained a preparation for application to the skin which has an excellent adhesiveness even when the base is applied thinly. Polyacrylic acid may be commercially available ones, preferably those having a viscosity of 5,000 to 150,000 cps at 25° C. in a 10% aqueous solution.

The above polyacrylic acid is usually contained in the adhesive gel base in an amount of 1 to 20%, preferably 3 to 15%. When the amount of polyacrylic acid is less than 1%, the desired three-dimensional network structure is not sufficiently formed and the formed gel becomes feeble. On the other hand, when the amount of polyacrylic acid is more than 20%, the drug-retaining layer becomes too hard, which results in a decreased adhesiveness or inhibition of transfer of the drug to the skin.

The crosslinking agent is used for crosslinking the above-mentioned polyacrylic acid dissolved in the lower alcohol or polyvalent alcohol to form a three-dimensional network structure to endow the base with a heat resistance so that the base does not melt out of the preparation when applied to human beings or during storage. The crosslinking agent used in the present invention includes aluminum salts and magnesium salts such as aluminum chloride, aluminum sulfate, aluminum potassiumsulfate, ammonium aluminum sulfate, magnesium aluminate silicate, magnesium aluminate metasilicate, dihydroxy aluminum acetate and the like, which may be used alone or in combination of two or more thereof. The crosslinking agent is usually used in an amount of 0.01 to 7%, preferably 0.01 to 5%, based on the amount of the adhesive gel base.

The lower alcohol or polyvalent alcohol acts as an agent for dissolving procaterol and/or the above-mentioned water-soluble high molecular weight compound or an agent for promoting drug delivery and includes, for example, lower alcohols such as ethanol, propanol, and the like; and polyvalent alcohols such as lower alkylene glycols (e.g. ethylene glycol, propylene glycol, 1,3-butanediol, 3-methyl-1,3-butanediol, and the like), poly(lower)alkylene glycols (e.g. polyethylene glycol, polypropylene glycol, and the like), glycerol, and the like, which may be used alone or in combination of two or more thereof. The "lower" alcohol in the specification means a $C_1$–$C_4$ alcohol.

The above-mentioned lower alcohol or polyvalent alcohol is usually used in an amount of 50 to 95%, preferably 55 to 90% based on the amount of the adhesive gel base. When the amount is less than 50%, the alcohols can not show the desired function as the agent for dissolving the above-mentioned water-soluble high molecular weight compound, and hence, the gel base shows an increased viscosity and becomes difficult to handle with. On the other hand, when the amount is more than 95%, amounts of the other components becomes excessively low, and as a result, basic characteristics of the preparation for application to the skin such as adhesiveness, shape retention, heat resistance, and the like cannot be obtained.

Polyacrylic acid or the crosslinking agent usually contains impurities such as a heavy metal or an ion thereof (e.g. aluminum, magnesium, or ion thereof). Accordingly, in order to promote the continuous decomposition of procaterol, the base may contain a sequestering agent to chelate the heavymetal, thereby stably preserving procaterol for a long period of time. The sequestering agent includes a conventional chelating agent capable of forming a chelate with the heavy metal or an ion thereof, including EDTA, a pharmaceutically acceptable salt of EDTA such as EDTA 2Na, polyphosphoric acid, a pharmaceutically acceptable salt of polyphosphoric acid such as potassium polyphosphate. The sequestering agent is used in an amount of 0.001 to 0.1% based on the amount of adhesive gel base.

As mentioned above, the adhesive gel base comprises polyacrylic acid, a crosslinking agent, and at least one lower alcohol or polyvalent alcohol as essential components. The adhesive gel base may further optionally contain a conventional high molecular weight compound, for example, sodium polyacrylate, polyvinyl alcohol, polyvinyl pyrrolidone, polyethylene oxide, sodium alginate, gelatine, dextrin, karaya gum, starch, etc., which is usually used in an amount of 0.01 to 7%, preferably 0.1 to 5%, based on the amount of the adhesive gel base.

The adhesive gel base may further optionally contain a conventional drug absorption-promoting agent (e.g. isopropyl myristate, isopropyl palmitate, N-methylpyrrolidone, N-ethylpyrrolidone, N,N-diethyl-m-toluamide, N,N-dimethylacetamide, hyaluronic acid, salicylic acid, chrotamiton, diethyl sebacate, lauryl alcohol, and the like) so that the drug is absorbed more efficiently. The absorption-promoting agent is used in an amount of 0.1 to 20% by weight, preferably 0.1 to 15% by weight, based on the amount of the adhesive gel base.

The amount of procaterol in the preparation is preferably determined under taking into consideration the application amount of the adhesive gel base so as to achieve high utilization degree of the drug. Generally speaking, it is preferred that the adhesive gel base is thinly applied to the skin and has a high concentration of the drug. From this point of view, procaterol is preferably contained in the adhesive gel base in an amount of 0.1 to 5%. When the amount is less than 0.1%, the activity of the drug cannot efficiently be exhibited. On the other hand, when the amount is more than 5%, the crosslinking of the base is inhibited and the heat resistance of the base becomes poor. Even if the adhesive gel base contains procaterol in an excessive amount, the drug is not effectively utilized and the activity of the drug is not improved, which is disadvantageous also from economical viewpoint.

The procaterol-containing preparation for application to the skin of the present invention can be prepared by dissolving polyacrylic acid in an alcohol with heating, cooling the solution, adding procaterol and other components thereto, and further adding a crosslinking agent thereto to prepare the adhesive gel base. The obtained adhesive gel base is then applied to a suitable support and laminate the surface with a liner to prepare a drug-retaining layer. The adhesive gel base is applied in an amount of less than 300 $g/m^2$, preferably 50 to 250 $g/m^2$.

The support used in the preparation of the invention is preferably made of a flexible thin material which fits for the movement of human body in order to prevent undesirable peeling when applied to the skin. The material used for the support includes, for example, various non-woven fabrics, woven fabrics, flannel, spandex, or a laminate thereof with polyethylene film, ethylene vinyl acetate film, polyurethane film, and the like.

The procaterol-containing preparation for application to the skin of the present invention prepared as mentioned above has the following characteristics:

(1) Since the preparation of the present invention contains a larger amount of alcohol in the base than that of conventional tapes or cataplasms, the drug is easily dissolved and dispersedly kept in the base, and hence, there can be prepared a base which shows an excellent drug delivery even when a small amount of the drug is contained in the base;

(2) Polyacrylic acid used in the base inhibits undesirable decomposition of the drug, allowing a stable storage of the drug for a long period of time;

(3) Since the drug dissolved is dispersedly retained within the adhesive gel base, the drug is delivered to the skin at a constant rate, allowing a continuous transdermal absorption;

(4) Since the base contains substantially no water, it is stable and hardly denatured when applied to the skin or during storage; and (5) The preparation of the present invention has a moderate adhesiveness, and hence, can be thinly applied. In addition, the preparation of the present invention does not cause pain when peeled off unlike tape preparation.

BEST MODE FOR CARRYING OUT THE INVENTION

Figure 1:
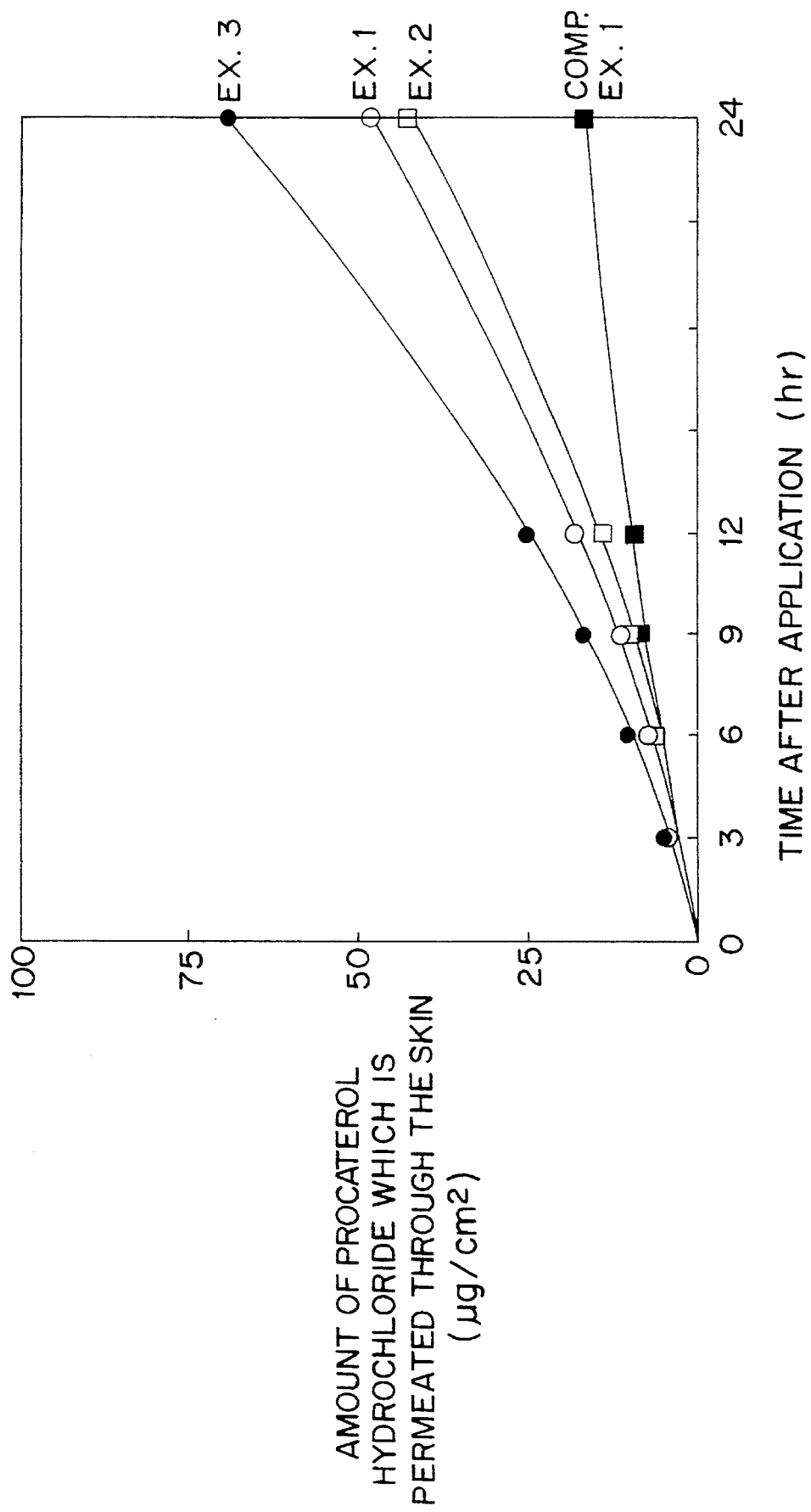
FIG. 1 is a graph showing a relationship between the time after application and the amount of procaterol hydrochloride which is permeated through the skin in the preparations for application to the skin prepared in Examples of the present invention and Comparative Example.

The preparation for application to the skin of the present invention is explained in more detail by means of Examples and Comparative Examples hereinbelow but should not be construed to be limited thereto.

EXAMPLE 1

| [Component] | [% (w/w)] |
|---|---|
| Polyacrylic acid (trade name Julimer AC-10HP manufactured by Nippon Junyaku K.K.) | 7 |
| Magnesium aluminate metasilicate | 2.5 |
| Procaterol hydrochloride | 0.5 |
| Propylene glycol | 30 |
| EDTA 2Na | 0.01 |
| Ethanol | 10 |
| Glycerol | q.s |
| Total | 100 |

Polyacrylic acid is dissolved in glycerol with heating at about 100° C. After cooling, thereto are added procaterol hydrochloride dissolved in propylene glycol and then the remaining components successively, and the mixture is stirred to give an adhesive base. Then, the adhesive gel base was applied to a support which is a laminate of non-woven fabric made of rayon and ethylene vinyl acetate film in an amount of 200 g/m². To the surface was adhered a liner made of polyethylene terephthalate film processed with silicone. The obtained preparation is cut into a desired size to give an external preparation for application to the skin (containing 100 µg/cm² of procaterol hydrochloride).

EXAMPLE 2

| [Component] | [% (w/w)] |
|---|---|
| Polyacrylic acid | 4 |
| Polyvinyl pyrrolidone (trade name PVP K-90 manufactured by G.A.F. CORPORATION) | 2 |
| Propylene glycol | 30 |
| Dihydroxy aluminum acetate | 1 |
| Aluminum potassium sulfate | 1.5 |
| Procaterol hydrochloride | 0.5 |
| EDTA 2Na | 0.01 |
| Glycerol | q.s |
| Total | 100 |

Using the above components, the procedures in Example 1 are repeated to give an external preparation for application to the skin (containing 100 µg/cm² of procaterol hydrochloride).

EXAMPLE 3

| [Component] | [% (w/w)] |
|---|---|
| Polyacrylic acid | 3 |
| Polyvinyl alcohol (trade name Gosenol NH-26 manufactured by the Nippon Synthetic Chemical Industry Co., Ltd.) | 3 |
| Propylene glycol | 20 |
| Magnesium aluminate metasilicate | 3 |
| Aluminum chloride | 0.5 |
| Procaterol hydrochloride | 1 |
| EDTA 2Na | 0.01 |
| N,N-diethyl-m-toluamide | 1 |
| Glycerol | q.s |
| Total | 100 |

Using the above components, the procedures in Example 1 are repeated except that the adhesive gel base is applied to the support at 100 g/m² to give an external preparation for application to the skin (containing 100 µg/cm² of procaterol hydrochloride).

EXAMPLE 4

| [Component] | [% (w/w)] |
|---|---|
| Polyacrylic acid | 7.04 |
| Magnesium aluminate metasilicate | 0.5 |
| Alum | 0.3 |
| Propylene glycol | 36.2 |
| N,N-diethyl-m-toluamide | 5 |
| N,N-dimethylacetamide | 10 |
| EDTA 2Na | 0.01 |
| Procaterol hydrochloride | 1 |
| Glycerol | q.s |
| Total | 100 |

Using the above components, the procedures in Example 1 are repeated to give an external preparation for application to the skin (containing 200 µg/cm² of procaterol hydrochloride).

EXAMPLE 5

| [Component] | [% (w/w)] |
|---|---|
| Polyacrylic acid | 6 |
| N,N-dimethylacetamide | 10 |
| Magnesium aluminate metasilicate | 3 |
| Procaterol hydrochloride | 1 |
| Propylene glycol | 20 |
| EDTA 2Na | 0.01 |
| Glycerol | q.s |
| Total | 100 |

Using the above components, the procedures in Example 1 are repeated to give an external preparation for application to the skin (containing 200 µg/cm² of procaterol hydrochloride).

EXAMPLE 6

| [Component] | [% (w/w)] |
|---|---|
| Polyacrylic acid | 6 |
| N,N-dimethylacetamide | 10 |
| Magnesium aluminate metasilicate | 3 |
| Procaterol hydrochloride | 1 |
| Propylene glycol | 20 |
| Glycerol | q.s |
| Total | 100 |

Using the above components, the procedures in Example 1 are repeated to give an external preparation for application to the skin (containing 200 µg/cm² of procaterol hydrochloride).

COMPARATIVE EXAMPLE 1

| [Component] | [% (w/w)] |
| --- | --- |
| Adhesive agent of emulsion type (copolymer of methyl acrylate and 2-ethylhexyl acrylate, solid content 60%) | 120 |
| Glycerol | 25 |
| N,N-diethyl-m-toluamide | 1 |
| Procaterol hydrochloride | 2 |
| Total | 148 |

Procaterol hydrochloride is dissolved in the above adhesive agent of emulsion type and then the remaining components are added thereto successively and the mixture is stirred. Thereafter, the obtained mixture is spread over a releasing paper in an amount of 100 g/m$^2$ (weight after dried) and dried. A polyethylene film is laminated onto the dried adhesive agent and the laminate product is cut into a desired size to give an external preparation for application to the skin (containing 200 µg/cm$^2$ of procaterol hydrochloride).

COMPARATIVE EXAMPLE 2

| [Component] | [% (w/w)] |
| --- | --- |
| Isobutylene-maleic anhydride copolymer (trade name: Isoban-10 manufactured by KURARAY CO. LTD.) | 20 |
| Glycerol polyglycidyl ether | 0.6 |
| Procaterol hydrochloride | 1 |
| Glycerol | q.s. |
| Total | 100 |

The isobutylene-maleic anhydride copolymer is added to glycerol and the mixture is stirred in a kneader at 55° C. for 50 minutes. Then, to the mixture are added procaterol hydrochloride and glycerol polyglycidyl ether in this order. However, the isobutylene-maleic anhydride copolymer is not dissolved in glycerol and remained therein as a dispersion, and as a result, any shaped preparation for application to the skin can not be obtained.

COMPARATIVE EXAMPLE 3

| [Component] | [% (w/w)] |
| --- | --- |
| Methyl vinyl ether-maleic anhydride copolymer (trade name: Gantrez, manufactured by G.A.F.) | 15 |
| Ethylene glycol diglycidyl ether | 1.3 |
| Procaterol hydrochloride | 1 |
| Glycerol | q.s. |
| Total | 100 |

The methyl vinyl ether-maleic anhydride copolymer is added to glycerol and the mixture was stirred in a kneader at 60° C. for 40 minutes. Then, to the mixture are added procaterol hydrochloride and ethylene glycol diglycidyl ether in this order. However, the methyl vinyl ether-maleic anhydride copolymer is not dissolved in glycerol and remained therein as a dispersion, and as a result, any shaped preparation for application to the skin can not be obtained.

COMPARATIVE EXAMPLE 4

| [Component] | [% (w/w)] |
| --- | --- |
| Isobutylene-maleic anhydride ammonium copolymer (trade name: Isoban-110 manufactured by KURARAY CO. LTD.) | 15 |
| Glycerol polyglycidyl ether | 0.5 |
| Procaterol hydrochloride | 1 |
| Glycerol | q.s. |
| Total | 100 |

The isobutylene-maleic anhydride ammoniumcopolymer is dissolved in glycerol at room temperature. To the solution are then added procaterol hydrochloride and glycerol polyglycidyl ether in this order and the mixture is stirred to give an adhesive base. Thereafter, the procedures in Example 1 are repeated to give an external preparation for application to the skin (containing 200 µg/cm$^2$ of procaterol hydrochloride).

COMPARATIVE EXAMPLE 5

| [Component] | [% (w/w)] |
| --- | --- |
| Methyl vinyl ether-maleic anhydride copolymer (trade name: Gantrez, manufactured by G.A.F.) | 15 |
| Ethylene glycol diglycidyl ether | 0.5 |
| Procaterol hydrochloride | 1 |
| Water | 40 |
| Glycerol | q.s. |
| Total | 100 |

The methyl vinyl ether-maleic anhydride copolymer is dissolved in glycerol with heating at 100° C. To the solution are then added procaterol hydrochloride, ethylene glycol diglycidyl ether in this order and the mixture is stirred to give an adhesive base. Thereafter, the procedures in Example 1 are repeated to give an external preparation for application to the skin (containing 200 µg/cm$^2$ of procaterol hydrochloride).

EXPERIMENT 1

The skin taken from rat abdomen was put in a Franz diffusion cell and each sample punched into a circular shape with 1.7 cm diameter (containing 227 µg of procaterol hydrochloride) was adhered to the rat skin in the diffusion cell (n=7). Using pH 7.0—phosphate buffer in a receptor, an amount of procaterol hydrochloride which permeated through the skin after a fixed time was measured by HPLC. The results are shown in FIG. 1.

EXPERIMENT 2

Figure 2:
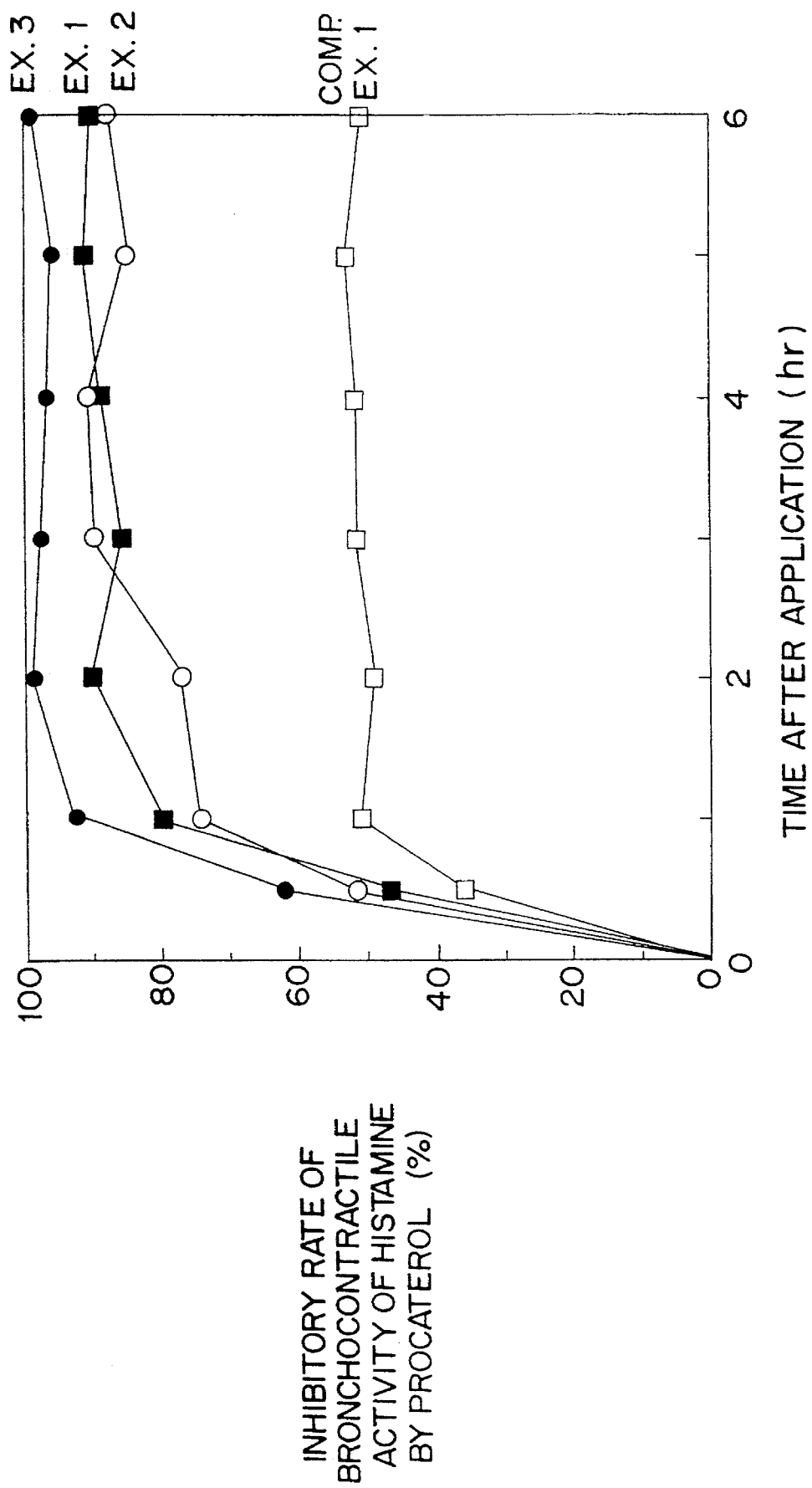
FIG. 2 is a graph showing a relationship between the time after application and the inhibitory rate of bronchocontractile activity of histamine by procaterol.

After anesthetizing dogs weighing 10 kg with pentobarbital, hair was removed at the abdomen and thereto was adhered the sample from Examples 1 to 3 (2×2 cm$^2$; containing 400 µg of procaterol hydrochloride) or from Comparative Example 1 (2×2 cm$^2$; containing 800 µg of procaterol hydrochloride). The bronchodilating activity was determined from a rate of inhibition to an increase of ventilation overflow by an intravenous administration of histamine (5 μg/kg), using the Konzett-Rossler method. The results are shown in FIG. 2.

EXPERIMENT 3

During the procedure in Experiment 2, blood was also taken from dogs and the cAMP level in their blood was measured by the EIA method. It is generally known that the formation of cAMP is promoted by the β-acceptor stimulating activity and the concentration of cAMP is directly proportional to blood level of β-acceptor stimulating agonist. The results are shown in Table 1.

TABLE 1

| Adhesion | Example | | | Comp. Example |
|---|---|---|---|---|
| Time (hr) | 1 | 2 | 3 | 1 |
| 0 | 11.4 | 16.5 | 10.9 | 10.5 |
| 0.5 | 26.7 | 23.3 | 27.8 | 18.8 |
| 1 | 38.5 | 33.5 | 43.2 | 19.0 |
| 3 | 39. | 38.0 | 53.6 | 23.4 |
| 6 | 38.7 | 36.2 | 52.6 | 21.7 |

Unit: pmol/ml

As is clear from the results of the above Experiments, it was found that the preparation for application to the skin of the present invention showed more excellent delivery, blood level and exhibition of activity of procaterol than those of the conventional emulsion type preparation for application to the skin.

We claim:

1. A procaterol-containing preparation for application to the skin which comprises a drug-retaining layer provided on a support, wherein said drug-retaining layer is a substantially water-free adhesive gel consists essential of 1 to 20% by weight of polyacrylic acid, a crosslinking agent selected from the group consisting of aluminum chloride, aluminum sulfate, aluminum potassium sulfate, ammonium aluminum sulfate, magnesium aluminate silicate, magnesium aluminate metasilicate, and dihydroxy aluminum acetate, 50 to 95% by weight of at least one lower alcohol or polyvalent alcohol, and 0.1 to 5% by weight of procaterol, or a pharmaceutically acceptable salt thereof.

2. The procaterol-containing preparation for application to the skin of claim 1 wherein said adhesive gel contains 1 to 20% by weight of said polyacrylic acid, 0.01 to 7% by weight of said crosslinking agent, and 50 to 95% by weight of said lower alcohol or polyvalent alcohol.

3. The procaterol-containing preparation for application to the skin of claim 1 wherein said adhesive gel contains 3 to 15% by weight of said polyacrylic acid, 0.01 to 5% by weight of said crosslinking agent, and 55 to 90% by weight of said lower alcohol or polyvalent alcohol.

4. The procaterol-containing preparation for application to the skin of claim 1 wherein said crosslinking agent is selected from the group consisting of an aluminum salt and a magnesium salt; said lower alcohol or polyvalent alcohol is selected from the group consisting of a lower alcohol, a lower alkylene glycol, poly(lower)alkylene glycol and glycerol.

5. The procaterol-containing preparation for application to the skin of claim 2 wherein said crosslinking agent is selected from the group consisting of an aluminum salt and a magnesium salt; said lower alcohol or polyvalent alcohol is selected from the group consisting of a lower alcohol, a lower alkylene glycol, poly(lower)alkylene glycol and glycerol.

6. The procaterol-containing preparation for application to the skin of claim 3 wherein said crosslinking agent is selected from the group consisting of an aluminum salt and a magnesium salt; said lower alcohol or polyvalent alcohol is selected from the group consisting of a lower alcohol, a lower alkylene glycol, poly(lower)alkylene glycol and glycerol.

7. The procaterol-containing preparation for application to the skin of claim 4 wherein said crosslinking agent is selected from the group consisting of aluminum chloride, aluminum sulfate, aluminum potassium sulfate, ammonium aluminum sulfate, magnesium aluminate silicate, magnesium aluminate metasilicate, and dihydroxy aluminum acetate; said lower alcohol is selected from the group consisting of ethanol and propanol; said polyvalent alcohol is selected from the group consisting of ethylene glycol, propylene glycol, 1,3-butanediol, 3-methyl-1,3-butanediol, polyethylene glycol, polypropylene glycol and glycerol.

8. The procaterol-containing preparation for application to the skin of claim 5 wherein said crosslinking agent is selected from the group consisting of aluminum chloride, aluminum sulfate, aluminum potassium sulfate, ammonium aluminum sulfate, magnesium aluminate silicate, magnesium aluminate metasilicate, and dihydroxy aluminum acetate; said lower alcohol is selected from the group consisting of ethanol and propanol; said polyvalent alcohol is selected from the group consisting of ethylene glycol, propylene glycol, 1,3-butanediol, 3-methyl-1,3-butanediol, polyethylene glycol, polypropylene glycol and glycerol.

9. The procaterol-containing preparation for application to the skin of claim 6 wherein said crosslinking agent is selected from the group consisting of aluminum chloride, aluminum sulfate, aluminum potassium sulfate, ammonium aluminum sulfate, magnesium aluminate silicate, magnesium aluminate metasilicate, and dihydroxy aluminum acetate; said lower alcohol is selected from the group consisting of ethanol and propanol; said polyvalent alcohol is selected from the group consisting of ethylene glycol, propylene glycol, 1,3-butanediol, 3-methyl-1,3-butanediol, polyethylene glycol, polypropylene glycol and glycerol.

10. The procaterol-containing preparation for application to the skin of claim 1, 2 or 3 wherein said crosslinking agent is selected from the group consisting of magnesium aluminate metasilicate, dihydroxy aluminum acetate and aluminum potassium sulfate, and said polyvalent alcohol is selected from the group consisting of propylene glycol and glycerol.

11. A procaterol-containing preparation for application to the skin which comprises a drug-retaining layer provided on a support, wherein said drug-retaining layer is a substantially water-free adhesive gel consists essential of 1 to 20% by weight of polyacrylic acid, a crosslinking agent selected from the group consisting of aluminum chloride, aluminum sulfate, aluminum potassium sulfate, ammonium aluminum sulfate, magnesium aluminate silicate, magnesium aluminate metasilicate, and dihydroxy aluminum acetate, a sequestering agent, 50 to 95% by weight of at least one lower alcohol or polyvalent alcohol, and 0.1 to 5% by weight of procaterol, or a pharmaceutically acceptable salt thereof.

12. The procaterol-containing preparation for application to the skin of claim 11 wherein said adhesive gel contains 1 to 20% by weight of said polyacrylic acid, 0.01 to 7% by weight of said crosslinking agent, 0.001 to 0.1% by weight of said sequestering agent and 50 to 95% by weight of said lower alcohol or polyvalent alcohol.

13. The procaterol-containing preparation for application to the skin of claim 11 wherein said adhesive gel contains 3 to 15% by weight of said polyacrylic acid, 0.01 to 5% by weight of said crosslinking agent, 0.001 to 0.1% by weight of said sequestering agent and 55 to 90% by weight of said lower alcohol or polyvalent alcohol.

14. The procaterol-containing preparation for application to the skin of claim 11 wherein said crosslinking agent is selected from the group consisting of an aluminum salt and a magnesium salt; said sequestering agent is a chelating agent; said lower alcohol or polyvalent alcohol is selected from the group consisting of a lower alcohol, a lower alkylene glycol, poly(lower)alkytene glycol and glycerol.

15. The procaterol-containing preparation for application to the skin of claim 12 wherein said crosslinking agent is selected from the group consisting of an aluminum salt and a magnesium salt; said sequestering agent is a chelating agent capable of forming a complex with a heavy metal or a heavy metal ion; said lower alcohol or polyvalent alcohol is selected from the group consisting of a lower alcohol, a lower alkylene glycol, poly(lower)alkylene glycol and glycerol.

16. The procaterol-containing preparation for application to the skin of claim 13 wherein said crosslinking agent is selected from the group consisting of an aluminum salt and a magnesium salt; said sequestering agent is a chelating agent capable of forming a complex with a heavymetal or a heavy metal ion; said lower alcohol or polyvalent alcohol is selected from the group consisting of a lower alcohol, a lower alkylene glycol, poly(lower)alkylene glycol and glycerol.

17. The procaterol-containing preparation for application to the skin of claim 14 wherein said crosslinking agent is selected from the group consisting of aluminum chloride, aluminum sulfate, aluminum potassium sulfate, ammonium aluminum sulfate, magnesium aluminate silicate, magnesium aluminate metasilicate, and dihydroxy aluminumacetate; said sequestering agent is selected from the group consisting of EDTA, a pharmaceutically acceptable salt of EDTA, polyphosphoric acid and a pharmaceutically acceptable salt of polyphosphoric acid; said alcohol is selected from the group consisting of ethanol and propanol; said polyvalent alcohol is selected from the group consisting of ethylene glycol, propylene glycol, 1,3-butanediol, 3-methyl-1,3-butanediol, polyethylene glycol, polypropylene glycol and glycerol.

18. The procaterol-containing preparation for application to the skin of claim 15 wherein said crosslinking agent is selected from the group consisting of aluminum chloride, aluminum sulfate, aluminum potassium sulfate, ammonium aluminum sulfate, magnesium aluminate silicate, magnesium aluminate metasilicate, and dihydroxy aluminum acetate; said sequestering agent is selected from the group consisting of EDTA, a pharmaceutically acceptable salt of EDTA, polyphosphoric acid and a pharmaceutically acceptable salt of polyphosphoric acid; said lower alcohol is selected from the group consisting of ethanol and propanol; said polyvalent alcohol is selected from the group consisting of ethylene glycol, propylene glycol, 1,3-butanediol, 3-methyl-1,3-butanediol, polyethylene glycol, polypropylene glycol and glycerol.

19. The procaterol-containing preparation for application to the skin of claim 16 wherein said crosslinking agent is selected from the group consisting of aluminum chloride, aluminum sulfate, aluminum potassium sulfate, ammonium aluminum sulfate, magnesium aluminate silicate, magnesium aluminate metasilicate, and dihydroxy aluminum acetate; said sequestering agent is selected from the group consisting of EDTA, a pharmaceutically acceptable salt of EDTA, polyphosphoric acid or a pharmaceutically acceptable salt of polyphosphoric acid; said lower alcohol is selected from the group consisting of ethanol and propanol; said polyvalent alcohol is selected from the group consisting of ethylene glycol, propylene glycol, 1,3-butanediol, 3-methyl-1,3-butanediol, polyethylene glycol, polypropylene glycol and glycerol.

20. The procaterol-containing preparation for application to the skin of claim 11, 12 or 13 wherein said crosslinking agent is selected from the group consisting of magnesium aluminate metasilicate, dihydroxy aluminum acetate and aluminum potassium sulfate, said polyvalent alcohol is selected from the group consisting of propylene glycol and glycerol, and said sequestering agent-is EDTA 2Na.

21. The procaterol-containing preparation for application to the skin of claim 11 which further comprises a drug absorption-promoting agent.

22. The procaterol-containing preparation for application to the skin of claim 12 which further comprises 0.1 to 20% by weight of an absorption-promoting agent.

23. The procaterol-containing preparation for application to the skin containing procaterol of claim 20 which further comprises 0.1 to 15% by weight of an absorption-promoting agent selected from the group consisting of N,N-diethyl-m-toluamide and N,N-dimethylacetamide.

\* \* \* \* \*

UNITED STATES PATENT AND TRADEMARK OFFICE
CERTIFICATE OF CORRECTION

PATENT NO. : 5,480,649
DATED : January 2, 1996
INVENTOR(S) : Akazawa et al.

It is certified that error appears in the above-identified patent and that said Letters Patent is hereby corrected as shown below:

Title page, item [73],

Please delete:

"Assignee:  Teikoku Seiaku Kabushiki Kaisha,
            Kagawa, Japan"

and replace with

--Assignee:  Teikoku Seiyaku Kabushiki Kaisha
             Kagawa-ken, Japan--

Signed and Sealed this

Ninth Day of April, 1996

Attest:

BRUCE LEHMAN

*Attesting Officer*   Commissioner of Patents and Trademarks